US008906605B2

(12) United States Patent (10) Patent No.: US 8,906,605 B2
Chen et al. (45) Date of Patent: Dec. 9, 2014

(54) ANALYTICAL METHOD OF POST-TRANSLATIONAL MODIFICATIONS IN HEMOGLOBIN

(71) Applicants: Hauh-Jyun Candy Chen, Chia-Yi (TW); Yu-Chin Chen, Taichung (TW)

(72) Inventors: Hauh-Jyun Candy Chen, Chia-Yi (TW); Yu-Chin Chen, Taichung (TW)

(73) Assignee: National Chung Cheng University, Chia-Yi (TW)

( * ) Notice: Subject to any disclaimer, the term of this patent is extended or adjusted under 35 U.S.C. 154(b) by 0 days.

(21) Appl. No.: 13/929,548

(22) Filed: Jun. 27, 2013

(65) Prior Publication Data
US 2014/0255964 A1    Sep. 11, 2014

(30) Foreign Application Priority Data

Mar. 7, 2013   (TW) .............................. 102108043 A

(51) Int. Cl.
 *C12Q 1/00*        (2006.01)
(52) U.S. Cl.
 USPC .................................. 435/4; 436/66; 436/89
(58) Field of Classification Search
 CPC ............ G01N 33/721; G01N 33/6818; G01N 33/6848
 USPC .......................................... 435/4; 436/66, 89
 See application file for complete search history.

(56) References Cited

U.S. PATENT DOCUMENTS

| 2004/0132638 | A1* | 7/2004 | Stamler et al. .................... 514/6 |
| 2011/0159016 | A1* | 6/2011 | Tezel et al. ................... 424/172.1 |
| 2013/0224755 | A1* | 8/2013 | Chen et al. .................... 435/6.14 |
| 2013/0295558 | A1* | 11/2013 | Chen et al. .................... 435/6.1 |

OTHER PUBLICATIONS

Chen H. et al. Reactive Nitrogen Oxide Species Induced Post Translational Modifications in Human Hemoglobin and the Association with Cigarette Smoking. Analytical Chemistry 84(18)7881-90, 2012.*
Chen H. et al. H2O2/Nitrite Induced Post Translational Modification of Human Hemoglobin Determined by MS. ChemBioChem 9(2)312-323, Jan. 25, 2008.*
Woodi M. et al. Analysis of Protein Postranslational Modifications by MS. Indian J of Clinical Biochemistry 24(1)23-29, 2009.*
Willard B. et al. Site Specific Quantitation of Protein Nitration Using LC/TMS. Analytical Chemistry 75(10)2370-6, 2003.*
Zhan X. et al. Nitroproteins from a Human Pituitary Adenoma Tissue Discovered with a Nitrotyrosine Affinity Column and Tandem MS. Analytical Biochemistry 354:279-289 2006.*
Proteomics in Investigation of Protein Nitration in Kidney Disease: Technical Challenges and Perspectives From the Spontaneously Hypertensive Rat, Tyther et al., Mass, Spectrometry Reviews 2011, 30, 121-141.
Nitroproteins from a human pituitary adenoma tissue discovered with a nitrotyrosine aYnity column and tandem mass spectrometry, Zhan et al., Analytical Biochemistry 354 (2006).
Proteomic method identifies proteins nitrated in vivo during inflammatory challenge, Aulak et al., PNAS, Oct. 9, 2001, vol. 98, No. 21, 12056-12061.
Site-Specific Quantitation of Protein Nitration Using Liquid Chromatography/Tandem Mass Spectrometry, Willard et al., Anal. Chem. 2003, 75, 2370-2376.
Selective Enrichment and Mass Spectrometric Identification of Nitrated Peptides Using Fluorinated Carbon Tags, Kim et al., Anal. Chem. 2011, 83, 157-163.
Apparent hydroxyl radical production by peroxynitrite: Implications for endothelial injury from nitric oxide and superoxide; Beckman et al, Proc. Nati. Acad. Sci. USA vol. 87, pp. 1620-1624, Feb. 1990
The chemistry of peroxynitritea: product from the reaction of nitric oxide with superoxide William; Pryor et al., Am J Physiol Lung Cell Mol Physiol 268:L699-L722, 1995.
Nitration of Unsaturated Fatty Acids by Nitric Oxide-Derived Reactive Nitrogen Species Peroxynitrite, Nitrous Acid, Nitrogen Dioxide, and Nitronium Ion; O'Donnell et al., Chem, Res. Toxicol. 1999, 12, 83-92.
Formation of nitric oxidederived inflammatory oxidants bymyeloperoxidase in neutrophils; Eiserich et al., Nature, vol. 391, Jan. 22, 1998.
Nitric oxide, oxidants, and protein tyrosine nitration, RADI, PNAS, Mar. 23, 2004, vol. 101, No. 12, pp. 4003-4008.
Effects of peroxynitrite-induced protein modifications on tyrosine phosphorylation and degradation, Gow et al., FEBS Letters 385 (1996) 63-66.
Peroxynitrite disables the tyrosine phosphorylation regulatory mechanism: Lymphocyte-specific tyrosine kinase fails to phosphorylate nitrated cdc2(6-20)NH2 peptide, Kong et al, Proc. Natl. Acad. Sci USA vol. 93, pp. 3377-3382, Apr. 1996.
Nitroproteins from a human pituitary adenoma tissue discovered with a nitrotyrosine affinity column and tandem mass spectrometry, Zhan et al., Analytical Biochemistry 354, pp. 279-289, 2006.
Nitrated and Oxidized Plasma Proteins in Smokers and Lung Cancer Patients, Pignatelli et al., Cancer Res 2001; 61:778-784.
Protein Tyrosine Nitration: Selectivity, Physicochemical and Biological Consequences, Denitration, and Proteomics Methods for the Identification of Tyrosine-Nitrated Proteins.
Journal of Proteome Research 2009, 8, 3222-3238.

\* cited by examiner

*Primary Examiner* — Ralph Gitomer
(74) *Attorney, Agent, or Firm* — Che-Yang Chen; Law Office of Michael Chen

(57) ABSTRACT

An analytical method of post-translational modifications in hemoglobin is disclosed. The analytical method comprises the steps of providing a blood comprising the hemoglobin with post-translational modification of nitration, nitrosylation, or oxidation; performing an extraction process to the blood by an organic solvent; quantifying the hemoglobin by a fluorescent spectrometry; hydrolyzing the hemoglobin into a plurality of peptides by an enzyme; and using a nanoflow liquid chromatography-nanospray ionization tandem mass spectrometry to characterize and quantify the post-translational modifications of the hemoglobin.

8 Claims, 6 Drawing Sheets

ANALYTICAL METHOD OF POST-TRANSLATIONAL MODIFICATIONS IN HEMOGLOBIN

CROSS-REFERENCE TO RELATED APPLICATION

This application claims priority from Taiwan Patent Application No. 102108043, filed on Mar. 7, 2013, the contents of which are hereby incorporated by reference in their entirety for all purposes.

BACKGROUND OF THE INVENTION

1. Field of the Invention

The present invention relates to an analytical method, and more particularly to the analytical method of post-translational modifications in hemoglobin.

2. Description of the Related Art

Excess production of nitrogen monoxide (NO) is found in inflamed tissues activated by neutrophils and phagocytes. In endogenous oxidative metabolism, nitrogen monoxide is reacted with reactive oxygen species (ROS) to form reactive nitrogen oxide species (RNOx) such as peroxynitrite, which is a biological nitration agent, leading to the formation of 3-nitrotyrosine (3NT) on protein [1]. ROS and RNOx may also react with other biomolecules in cells to produce chemical modifications of different types, including deoxyribonucleic acid (DNA) and lipid [2-3]. Peroxynitrite is not the only source of 3NT in vivo, and peroxidase and certain metalloproteins [4] may also cause the formation of 3NT.

3-nitrotyrosine (3NT) in vivo has been detected under several pathological or physiological conditions. Inflammation and neurodegenerative diseases are correlated with nitration of tyrosine [5]. However, compared to protein phosphorylation, the nitration of tyrosine in cells may not be modified easily. In the normal content of 3-nitrotyrosine (3NT) in vivo, there is one 3NT in every approximately $10^6$ tyrosine; and in an inflammation, there is one 3NT in every $10^4$ tyrosine [5].

The nitration of tyrosine in post-translational protein directly leads to inhibition of protein functions or inhibition of tyrosine phosphorylation [6,7]. The nitration of tyrosine is not a permanent modification, and it can be reversed under redox control. Present literatures show that smokers and lung cancer patients have contents of protein nitration and oxidation in serum protein higher than those of normal persons [8,9], indicating that oxidation and nitration pressure play an important role in smoking and cancer development process [10]. Literatures [8,9] also point out that protein 3-NT can be quantified by western blotting, but this method does not provide high accuracy or specific measurement. The advancement of proteomics based on mass spectrometry can perform analyses by focusing on the identification of a specific nitrated protein and the position of a modified amino acid [11]. Since the nitrated tyrosine protein in vivo has a very low content, therefore the antibody of 3-NT is generally used to concentrate the content of protein including 3-NT before the western blotting or mass spectrometry takes place [12]. Other concentration methods including a series of reactions and derivatizations are developed extensively for the analysis of proteomics to overcome the problem of detecting a low content of nitrated protein [9, 13-15].

REFERENCE AND LITERATURE (1) Beckman, J. S.; Beckman, T. W.; Chen, J.; Marshall, P. A.; Freeman, B. Proc. Natl. Acad. Sci. U.S.A. 1990, 87, 1620-1624.

(2) Pryor, W. A.; Squadrito, G. L. Am. J. Physiol. 1995, 268, L699-722.

(3) O'Donnell, V. B.; Eiserich, J. P.; Chumley, P. H.; Jablonsky, M. J.; Krishna, N. R.; Kirk, M.; Barnes, S.; Darley-Usmar, V. M.; Freeman, B. A. Chem. Res. Toxicol. 1999, 12, 83-92.

(4) Eiserich, J. P.; Hristova, M.; Cross, C. E.; Jones, A. D.; Freeman, B. A.; Halliwell, B.; van der Vliet, A. Nature 1998, 391, 393-397.

(5) Radi, R. Proc. Natl. Acad. Sci. U.S.A. 2004, 101, 4003-4008.

(6) Gow, A. J.; Duran, D.; Malcolm, S.; Ischiropoulos, H. FEBS Lett. 1996, 385, 63-66.

(7) Kong, S.-K.; Yim, M. B.; Stadtman, E. R.; Chock, P. B. Proc. Natl. Acad. Sci. U.S.A. 1996, 93, 3377-3382.

(8) Gole, M. D.; Souza, J. M.; Choi, I.; Hertkorn, C.; Malcolm, S.; Foust, R. F., III; Finkel, B.; Lanken, P. N.; Ischiropoulos, H. Am. J. Physiol. Lung Cell Mol. Physiol. 2000, 278, L961-967.

(9) Pignatelli, B.; Li, C. Q.; Boffetta, P.; Chen, Q.; Ahrens, W.; Nyberg, F.; Mukeria, A.; Bruske-Hohlfeld, I.; Fortes, C.; Constantinescu, V.; Ischiropoulos, H.; Ohshima, H. Cancer Res. 2001, 61, 778-784.

(10) Abello, N.; Kerstjens, H. A. M.; Postma, D. S.; Bischoff, R. J. Proteome Res. 2009, 8, 3222-3238.

(11) Tyther, R.; McDonagh, B.; Sheehan, D. Mass Spectrom. Rev. 2010, 30, 121-141.

(12) Zhan, X.; Desiderio, D. M. Anal. Biochem. 2006, 354, 279-289.

(13) Aulak, K. S.; Miyagi, M.; Yan, L.; West, K. A.; Massillon, D.; Crabb, J. W.; Stuehr, D. J. Proc. Natl. Acad. Sci. U.S.A. 2001, 98, 12056-12061.

(14) Willard, B. B.; Ruse, C. I.; Keightley, J. A.; Bond, M.; Kinter, M. Anal. Chem. 2003, 75, 2370-2376.

(15) Kim, J. K.; Lee, J. R.; Kang, J. W.; Lee, S. J.; Shin, G. C.; Yeo, W.-S.; Kim, K.-H.; Park, H. S.; Kim, K. P. Anal. Chem. 2011, 83, 157-163.

SUMMARY OF THE INVENTION

In view of the aforementioned technical problems, it is a primary objective of the present invention to provide an analytical method of post-translational modifications in hemoglobin to overcome the drawbacks of the western blotting having low quantitative specificity and accuracy.

To achieve the aforementioned objective, the present invention provides an analytical method of post-translational modifications in hemoglobin to simplify the conventional complicated procedure of quantifying nitrated protein by antibody.

Another objective of the present invention is to provide an analytical method of post-translational modifications in hemoglobin to simplify the complexity of the conventional standard quantification of nitrated protein by isotopes.

To achieve the aforementioned objectives, the present invention provides an analytical method of post-translational modifications in hemoglobin, comprising the steps of: providing a blood comprising a hemoglobin, wherein the hemoglobin has a post-translational modification (PTM) of nitration, nitrosylation, or oxidation; performing an extraction process to the blood by an organic solvent; quantifying the hemoglobin by a fluorescent spectrometry; hydrolyzing the hemoglobin into a plurality of peptides by an enzyme; and using a nanoflow liquid chromatography-nanospray ionization tandem mass spectrometry (nanoLC-NSI/MS/MS) to characterize and quantify the post-translational modifications of the hemoglobin.

Preferably, the blood has a volume of 10 μL.

Preferably, the organic solvent is isopropanol, ethyl acetate or n-hexane.

Preferably, the enzyme is trypsin.

Preferably, the post-translational modification of nitration of the hemoglobin comprises tyrosine 24 and tyrosine 42 on α chain and tyrosine 130 on β chain of the amino acid sequence of the hemoglobin.

Preferably, the nanoflow liquid chromatography-nanospray ionization tandem mass spectrometry has a spray voltage from 1.3 kV to 2.0 kV.

Preferably, the nanoflow liquid chromatography-nanospray ionization tandem mass spectrometry has an ion transfer tube with a heating temperature from 200° C. to 300° C.

Preferably, the nanoflow liquid chromatography-nanospray ionization tandem mass spectrometry further comprises collision energy, and the collision energy ranges from 10% to 35% after being normalized.

Preferably, nanoflow liquid chromatography-nanospray ionization tandem mass spectrometry has an analysis mode being a selected reaction monitoring (SRM) mode.

The present invention further provides an analytical method of smoking related diseases, and this analytical method uses the analysis result of the aforementioned post-translational modification of nitration as a biological indicator to evaluate the nitrification condition in a living organism so as to achieve a diagnostic analysis of smoking related diseases.

In summation, the analytical method of post-translational modifications in hemoglobin and its applications in accordance with the present invention have one or more of the following advantages:

(1) The analytical method of the present invention can characterize and quantify a plurality of post-translational modifications in hemoglobin to achieve the effects of reducing the analytical time, saving manpower and avoiding unnecessary waste of consumables.

(2) The analytical method of the present invention has a high sensitivity and just requires a small quantity of sample for the analysis.

DESCRIPTION OF THE PREFERRED EMBODIMENTS

Figure 1:
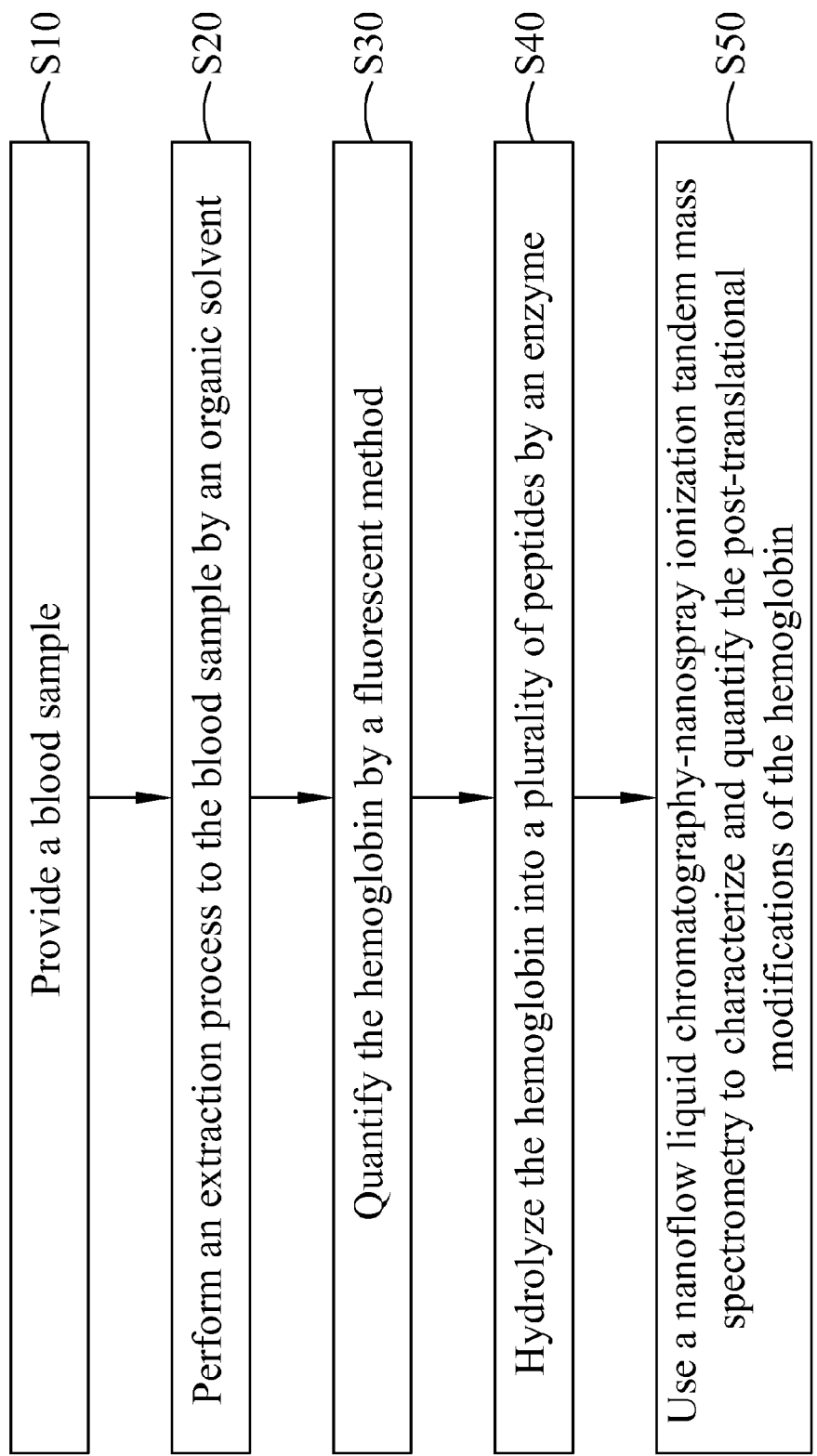
FIG. 1 is a flow chart of a preferred embodiment of the present invention.

With reference to FIG. 1 for a flow chart of an analytical method of a preferred embodiment of the present invention, the analytical method comprises the following steps:

S10: Provide a blood sample.

S20: Perform a hemoglobin extraction process to the blood sample by an organic solvent.

S30: Quantify the hemoglobin by a fluorescence method.

S40: Hydrolyze the hemoglobin into a plurality of peptides by an enzyme.

S50: Use a nanoflow liquid chromatography-nanospray ionization tandem mass spectrometry to characterize and quantify the post-translational modifications of the hemoglobin.

Experimental Method: Reaction of Human Hemoglobin with Peroxynitrite

A total volume of 0.2 mL of ammonium bicarbonate (25 mM) solution containing 0.1 mM human hemoglobin and 15 mM peroxynitrite purchased from Sigma Company was incubated at room temperature for 10 minutes under a nitrogen atmosphere. A portion of the volume (7.8 μL, equivalent to 50 μg of hemoglobin) was removed from the mixture and added into cold acetone (80 μL) and maintained at −20° C. for 15 minutes, and then centrifuged at 0° C. for 20 minutes, wherein the centrifugal force was set to 23000 xg. The supernatant was removed, and the precipitate was air-dried.

Enzyme Digestion

The precipitated hemoglobin was dissolved in deionized water, and the following fluorescent quantitative method was used for the quantification. An equivalent to 50 μg of hemoglobin were dissolved in 80 μL of deionized water, and 10 μL of ammonium bicarbonate (with a final concentration 100 mM and pH 8.0) and 10 μL of sodium dodecyl sulfate (SDS) (with a final concentration 1.0%) were added and reacted at 95° C. for 10 minutes. Cold acetone (900 μL) was added into the mixture and sits still at −20° C. for 15 minutes, and then centrifuged for 20 minutes, wherein the centrifugal force was set at 23000 xg. Trypsin (with a specific ratio 10:1, a volume 50 μL, and a weight 5 μg) was added into the precipitate and hydrolyzed at 37° C. for 18 hours. Trifluoroacetic acid (0.1%, 50 μL) was added into the reacting mixture to terminate the hydrolysis reaction. Trypsin digest was passed through a 0.22 μm nylon syringe filter, and 4 μL of the solution was injected into a nanoLC-NSI/MS/MS system.

In experiments with reduction/alkylation, a total volume of 100 μL of aqueous solution containing 50 μg of hemoglobin, ammonium bicarbonate (100 mM, pH8.0), SDS(1.0%) and dithiothreitol (DTT) (10 mM), was incubated at 95° C. for 10 minutes, followed by alkylation with iodoacetic acid (IAA) (500 mM, 11 μL) with shaking at room temperature in the dark for 1 hour. As described above, the solution was precipitated by cold acetone and digested into peptide by trypsin.

Accurate Mass Analysis

The human hemoglobin solution reacted with peroxynitrite (15 mM) was digested with trypsin, precipitated as describes above, and reconstituted in 100 μL of 0.1% trifluoroacetic acid before analysis by a reversed phase nanoLC system connected to an LTQ Orbitrap XL (Thermo Fisher Scientific, San Jose, Calif.). The peptides were analyzed in the positive ion mode by nanospray ionization source of a nanospray voltage of 1.6 kV. The mass spectrometry was operated in a data-dependent scan mode, wherein one full scan with m/z 300-2000 in the Orbitrap at a resolution of 60,000 at m/z 400 using a rate of 30 ms/scan. After every full scan of the LTQ, the first five strong signals were selected for fragmentation, and the normalized collision energy is 35%.

The proteins were identified by using a MASCOT v2.3.02 search engine on the Swiss-Prot 56 human protein database. The mass tolerance of precursor was set to be 5 ppm, and the mass tolerance of product ions was set to be 0.8 Da. All MS/MS spectra were searched against the database for characterizing variable modifications including the oxidation of methionine (+16), cysteine (+32 or +48), nitrosylation (+29), and nitration (+45) of tyrosine or tryptophan residues, and one missed cleavage on trypsin was allowed. The threshold of comparison score was set to 20 (p<0.05) to eliminate the low score peptides, and only "rank 1" (best match for each MS/MS) peptides were included.

Nanoflow Liquid Chromatography-nanospray Ionization Tandem Mass spectrometry (NanoLC-NSI/MS/MS)

A volume of 4 µL of each sample was injected onto an LC system consisting of an UltiMate 3000 RSLC nano system (Dionex, Amsterdam, Netherlands) and a C18 precolumn (100 µm×20 mm) packed in-house (Magic C18, 5 µm, 100 Å, Michrom BioResource, Auburn, Calif.), followed by separation using a C18 analyzing column (75 µm×120 mm) packed in-house (Magic C18AQ, 5 µm, 200 Å, Michrom BioResource, Auburn, Calif.). Mobile phases of A and B were composed of 5% and 80% acetonitrile in 0.1% formic acid (pH 2.6), respectively. The elution system started with 4% B for the first 2 minutes, followed by a linear gradient from 4% B to 40% B in the next 38 minutes and from 40% B to 90% B in the next 20 minutes, maintained at 90% B for another 10 minutes at a flow rate of 300 mL/min. The conditions were equilibrated with 4% B for 20 minutes before the next run. The column was coupled to an LTQ linear ion trap mass spectrometry (Thermo Electron Corp., San Jose, Calif.) fitted with a nanospray ionization (NSI) source. All mass spectrometry experiments for peptide characterization were performed at a heated capillary temperature of 200° C. with a capillary voltage of 2.0V, a source voltage of 1.5 kV, a tube lens voltage of 70V, a source current of 100 µA, a normalized collision energy setting of 35%, and the internal pressure of the mass spectrometry setting of $6.4 \times 10^{-6}$ torr.

Sequence Database Search and Data Analysis

To identify sites of modifications, the hemoglobin (0.1 mM) reacted with peroxynitrite (15 mM) was precipitated to remove excess reagent and digested with trypsin as described above. Under the data-dependent scan mode, the full mass spectrometry scan (m/z 350-2000) and the secondary mass spectrometry used for the nine most abundant signals were switched automatically. Ions with a charge state of 4 and higher were excluded. Peptide fingerprinting from the MS/MS data was performed with the aid of the TurboSE-QUEST system incorporated in BioWorks version 3.3 (by Thermo Electron Corp., San Jose, Calif.) to correlate the data against the NCBI protein database (National Center for Biotechnology Information, Bethesda, Md.) with the following parameters: threshold, 1000; group scan tolerance, 1; minimum group count 1; precursor charge state, auto; MS' level, auto. Monoisotopic mass was used for the search, and the mass tolerance of peptides and fragment ions was set at 0.5 amu.

Semiquantification of Modified Peptide

The selected reaction monitoring (SRM) experiments were performed by selecting the precursor ion and collecting the full-scan daughter ion spectra. The formation of a specific fragment ion from each precursor ion was used to construct the chromatogram. The specific SRM conditions for peptides containing tyrosine, methionine, cysteine and their modifications are listed in Table 1, wherein the symbol "" represents modified ion, and unmodified peptides or reference peptides were represented by bold font. The extent of modification on a specific peptide was calculated as the signal peak area of the modified peptide versus the sum of the peak areas of the modified peptide and the corresponding reference (unmodified) peptide in the SRM chromatograms.

TABLE 1

| AA start-end | peptides from α-globin | parent ion (m/z) | daughter ion (m/z) |
|---|---|---|---|
| 17-31 | VGAHAGE$^{24}$Y$^{NO2}$GAEALER | 787.8 (+2) | 1139.5 (+1, $y_{10}'$) |
| 17-31 | VGAHAGE$^{24}$Y$^{NO}$GAEALER | 779.9 (+2) | 1123.5 (+1, $y_{10}'$) |
| 17-31 | VGAHAGEYGAEALER | 765.4 (+2) | 1094.5 (+1, $y_{10}$) |
| 32-40 | $^{32}$M$^{O}$FLSFPTTK | 544.4 (+2) | 793.5 (+1, $y_7$) |
| 32-40 | MFLSFPTIK | 536.3 (+2) | 793.5 (+1, $y_7$) |
| 41-56 | T$^{42}$Y$^{NO2}$FPHFDLSHGSAQVK | 940.0 (+2) | 711.9 (+2, $y_{13}$) |
| 41-56 | TYFPHFDLSHGSAQVK | 917.5 (+2) | 711.9 (+2, $y_{13}$) |
| 62-90 | VADALTNAVAHVDD$^{76}$M$^{O}$PNALSALSDLHAHK | 1004.8 (+3) | 1078.6 (+1, $y_{10}$) |
| 62-90 | VADALTNAVAHVDDMPNALSALSDLHAHK | 999.5 (+1) | 1078.6 (+1, $y_{10}$) |
| 100-127 | LLSH$^{104}$C$^{O3}$LLVTLAAHLPAEFTPAVHASLDK | 1005.9 (+3) | 1151.1 (+2, $y_{22}$) |
| 100-127 | LLSH$^{104}$C$^{O2}$LLVTLAAHLPAEFTPAVHASLDK | 1000.5 (+3) | 1151.1 (+2, $y_{22}$) |
| 41-56 | TYFPHFDLSHGSAQVK | 917.5 (+2) | 711.9 (+2, $y_{13}$) |
| | peptides from β-globin | | |
| 41-59 | FFESFGDLSTPDAV$^{55}$M$^{O}$GNPK | 1038.0 (+2) | 944.5 (+1, $y_9'$) |
| 41-59 | FFESFGDLSTPDAVMGNPK | 1030.2 (+2) | 928.5 (+1, $y_9$) |
| 83-95 | GTFATLSELH$^{93}$C$^{O3}$DK | 735.4 (+2) | 879.4 (+1, $y_7'$) |
| 18-30 | VNVDEVGGEALGR | 657.8 (+2) | 758.3 (+1, $y_8$) |
| 105-120 | LLGNVLV$^{112}$C$^{O3}$VLAHHFGK | 884.5 (+2) | 1059.5 (+1, $y_9'$) |
| 67-82 | VLGAFSDGLAHLDNLK | 835.5 (+2) | 980.4 (+1, $y_9$) |
| 121-132 | EFTPPVQAA$^{130}$Y$^{NO2}$QK | 712.4 (+2) | 523.8 (+2, $y_9^{2+}$) |
| 121-132 | EFTPPVQAAYQK | 690.1 (+2) | 501.3 (+2, $y_9^{2+}$) |

Dose-Dependence of the Extents of PTM by Peroxynitrite or Hydrogen Oxide Concentration Samples of commercial human hemoglobin (0.1 mM) reacted with various concentrations of peroxynitrite (0, 10, 20, 80, or 100 µM) in ammonium bicarbonate (25 mM) and potassium phosphate buffer (0.1M, pH7.4) at room temperature for 10 minutes were analyzed as described above. The experiments were performed in triplicates for each concentration. The dose-dependence was plotted as the peak area of the signal versus the concentration of hydrogen peroxide.

Isolation of Hemoglobin from Fresh Blood

The blood samples (10 µL) were collected fresh in a tube containing 10% (by volume) citrate-dextrose solution as an anticoagulant and centrifuged (800×g, 10 minutes, 10° C.) to separate red blood cells from serum. The isolated hemoglobin was dissolved in water and quantified by interpolation to a calibration curve constructed from solution containing various concentrations (0.02, 0.04, 0.06, 0.08 and 0.1 µg/µL) of standard human hemoglobin (100 µM) from Sigma Chemical Co. in hydrochloric acid (50 mM) and measured by the tryptophan-induced fluorescence at the excitation and emission wavelength at 280 and 353 nm, respectively.

Study-Subjects

The study-subjects of the present invention were healthy adults recruited from employees and students of the National Chung Cheng University, including 20 male smokers and 20 non-smokers (11 males and 9 females). The mean (±standard deviation (SD)) age was 23.5±5.9 for smokers and 25.0±6.5 for non-smokers. The mean smoking index (number of cigarette per day×years smoked) of the study-subjects was 38.4±67.9 and all smokers have a smoking index within a range of 0~300.

Statistical Analysis

GraphPad InStat version 3.00 (GraphPad Software, San Diego, Calif.) was used for the statistical analysis. The non-parametric Mann-Whitney test was used for analyzing the extent of each modification between the 20 smokers and 20 non-smokers.

Result and Discussion

The abundance of modified peptides in human blood is very low; thus, a hemoglobin sample was treated with peroxynitrite to obtain high extents of medications for characterization purpose.

Accurate Mass Analysis of Post-translational Modifications in Peroxynitrite-treated Hemoglobin The qualitative analysis of the post-translational modifications of the human hemoglobin by using peroxynitrite for the reaction was performed by using the shotgun approach under the data-dependent scan mode. In this sample, human hemoglobin (0.1 mM) was reacted with peroxynitrite (15 mM) in the presence of physiological concentration of bicarbonate (25 mM) solution. To avoid misidentifying the modified peptides, the mass error of peptide ions was set below 5 ppm and that for fragment ions was 0.8Da. In this experiment, a total of 11 types of modified peptides are identified, and the difference between experimental and calculated theoretical mass was within a range from 0.0001 to 0.0097. The threshold score was set to 20 and the scores of these modified peptides were greater than 25. As to the amino acid sequence coverage of the sample, α-hemoglobin is 96% and β-hemoglobin is 89%. As listed in Table 2, a total of 11 modifications were identified, including nitration on three tyrosine residues and nitrosylation on 1 tyrosine. As to the oxidation, three methionine residues were oxidized into sulfoxide and cysteine residue was oxidized into sulfonic acid and sulfinic acid.

TABLE 2

| AA start-end | | m/z exptl | z | M exptl | M calcd | ΔM | score | modification |
|---|---|---|---|---|---|---|---|---|
| | peptides from α-globin | | | | | | | |
| 17-31 | VGAHAGE$^{24}$Y$^{NO}$GAEALER | 779.8697 | 2 | 1557.7248 | 1557.7171 | 0.0077 | 27.73 | −H + NO ($Y_1$ + 29) |
| 17-31 | VGAHAGE$^{24}$Y$^{NO2}$GAEALER | 787.8639 | 2 | 1573.7132 | 1573.7121 | 0.0011 | 77.47 | −H + NO$_2$ ($Y_1$ + 45) |
| 17-31 | VGAHAGE$^{24}$YGAEALER | 765.3706 | 2 | 1528.7267 | 1528.7270 | −0.0003 | 80.82 | |
| 32-40 | $^{32}$M$^O$FLSFPTTK | 544.2793 | 2 | 1086.5441 | 1086.5420 | 0.0021 | 40.73 | + O ($M_1$ + 16) |
| 32-40 | $^{32}$MFLSFPTTK | 536.281 | 2 | 1070.5474 | 1070.5471 | 0.0003 | 50.45 | |
| 41-56 | T$^{12}$Y$^{NO2}$FPHFDLSHGSAQVK | 939.9441 | 2 | 1877.8736 | 1877.8697 | 0.0039 | 42.19 | −H + NO$_2$ ($Y_1$ + 45) |
| 41-56 | T$^{12}$YFPHFDLSHGSAQVK | 917.4507 | 2 | 1832.8869 | 1832.8846 | 0.0023 | 101.2 | |
| 62-90 | VADALTNAVAHVDD$^{76}$M$^O$PNALSALSDLHAHK | 1004.8362 | 3 | 3011.4868 | 3011.4771 | 0.0097 | 79.21 | + O ($M_1$ + 16) |
| 62-90 | VADALTNAVAHVDD$^{76}$MPNALSALSDLHAHK | 999.5024 | 3 | 2995.4854 | 2995.4821 | 0.0033 | 126.2 | |
| 100-127 | LLSH$^{104}$C$^{O2}$LLVTLAAHLPAEFTPAVHASLDK | 1000.5417 | 3 | 2998.6032 | 2998.5950 | 0.0082 | 29.55 | + O$_2$ ($C_1$ + 32) |
| 100-127 | LLSH$^{104}$C$^{O3}$LLVTLAAHLPAEFTPAVHASLDK | 1005.8714 | 3 | 3014.5923 | 3014.5899 | 0.0024 | 41.85 | + O$_3$ ($C_1$ + 48) |
| | peptides from β-globin | | | | | | | |
| 41-59 | FFESFGDLSTPDAV$^{55}$M$^O$GNPK | 1037.9765 | 2 | 2073.9385 | 2073.9354 | 0.0031 | 78.06 | + O ($M_1$ + 16) |
| 41-59 | FFESFGDLSTPDAV$^{55}$MGNPK | 1029.9773 | 2 | 2057.9400 | 2057.9405 | −0.0005 | 106.7 | |
| 83-95 | GTFATLSELH$^{93}$C$^{O3}$DK | 735.3325 | 2 | 1468.6505 | 1468.6504 | 0.0001 | 56.38 | + O$_3$ ($C_1$ + 48) |
| 83-95 | GTFATLSELH$^{93}$CDK | 711.3382 | 2 | 1420.6619 | 1420.6657 | −0.0038 | 45.06 | |
| 105-120 | LLGNVLV$^{112}$C$^{O3}$VLAHHFGK | 884.4833 | 2 | 1766.9521 | 1766.9502 | 0.0020 | 59.88 | + O$_3$ ($C_1$ + 48) |
| 121-132 | EFTPPVQAA$^{130}$Y$^{NO2}$QK | 712.3480 | 2 | 1422.6815 | 1422.6779 | 0.0036 | 50.74 | −H + NO$_2$ ($Y_1$ + 45) |
| 121-132 | EFTPPVQAA$^{130}$YQK | 689.8534 | 2 | 1377.6923 | 1377.6929 | −0.0005 | 68.94 | |

Tyrosine Nitration and Nitrosylation

In the six tyrosine residues in human hemoglobin, the nitrations of tyrosine 24 on a chain (α-Tyr-24), tyrosine 42 on a chain (α-Tyr-42) and tyrosine 130 on β chain (β-Tyr-130) and the nitrosylation of tyrosine 24 on a chain (α-Tyr-24) were observed after trypsin was digested.

After trypsin was digested, α-Tyr-140 and β-Tyr-145 residues were in the dipeptides located at the C-termini of the α- and β-hemoglobin, respectively. Since these dipeptides were not retained in the LC system, therefore we were unable to characterize them. The nitrated peptide containing Tyr-35 (β-hemoglobin) as well as the unmodified peptide was one of the few peptides not detected after trypsin is digested.

Figure 2:
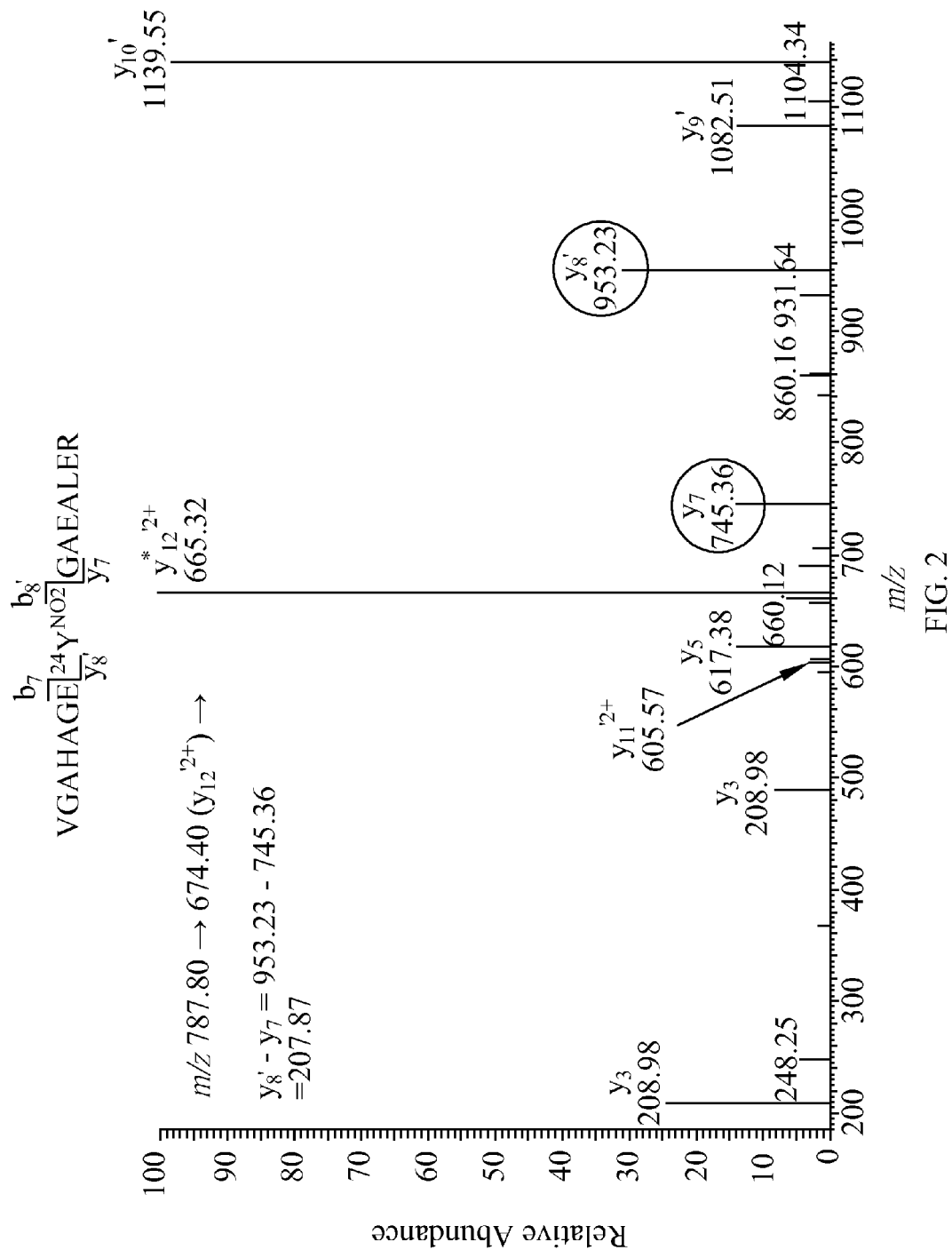
FIG. 2 shows a $MS^3$ scan spectrum of 3-nitrotyrosine-containing peptides of a preferred embodiment of the present invention.
Figure 3:
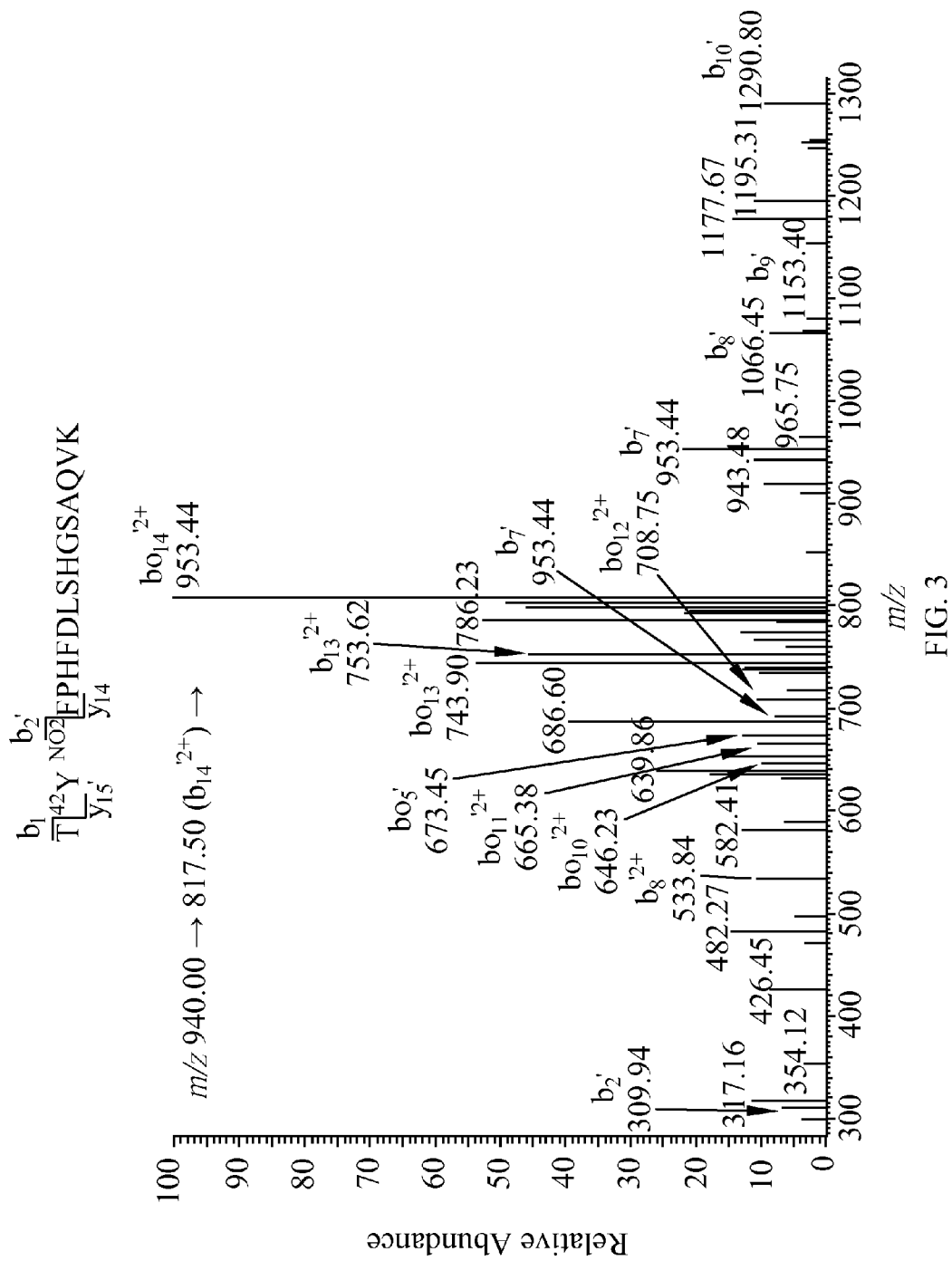
FIG. 3 shows a $MS^3$ scan spectrum of 3-nitrotyrosine-containing peptides of a preferred embodiment of the present invention.
Figure 4:
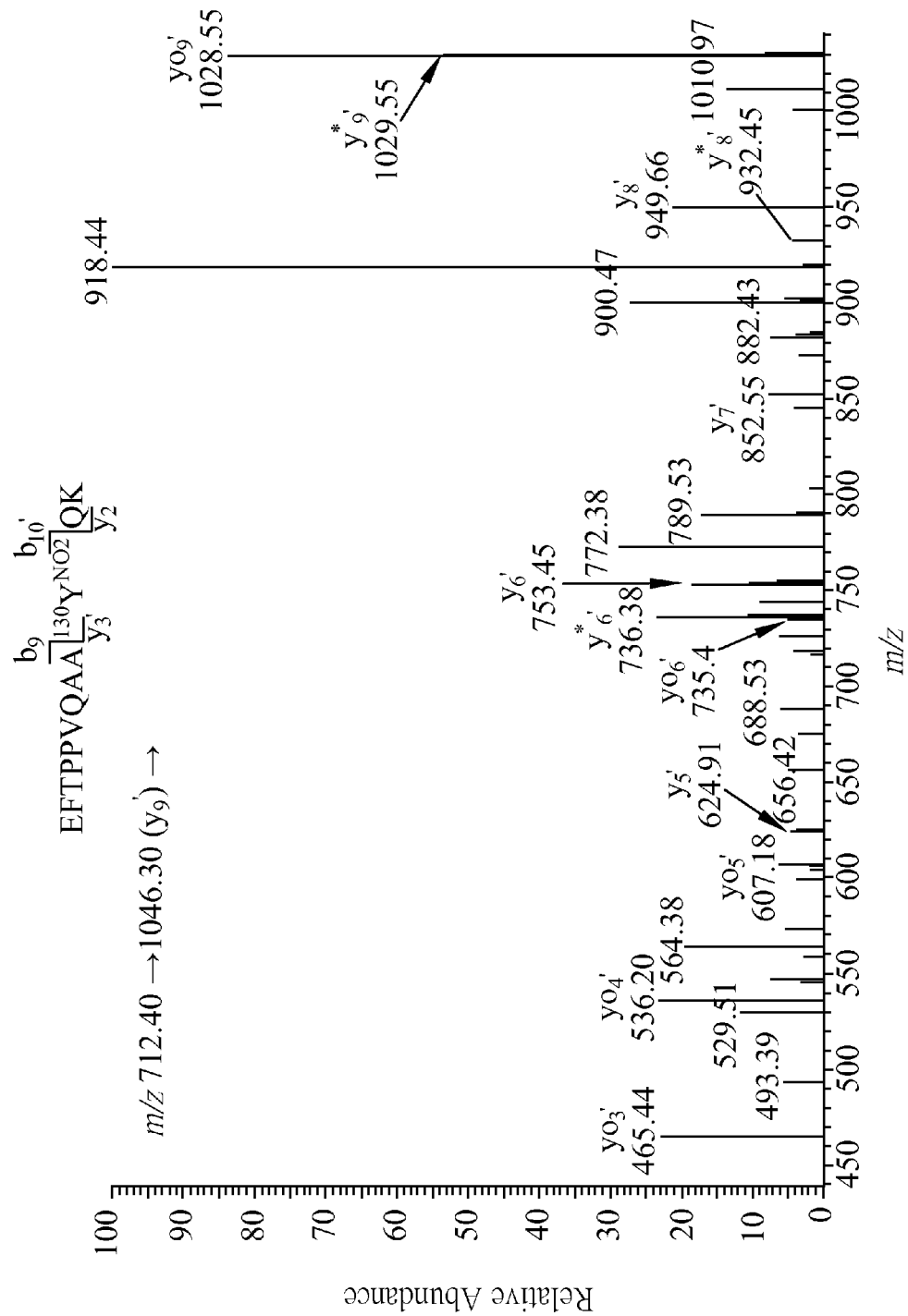
FIG. 4 shows a $MS^3$ scan spectrum of 3-nitrotyrosine-containing peptides of a preferred embodiment of the present invention.

As shown in FIGS. 2 to 4, several fragment ions with a mass shift of +45 or +28 (M—H+NO$_2$—NH$_3$) or +27 (M—H+NO$_2$—H$_2$O) provide a nitration evidence on the tyrosine residues (α-Tyr-24, α-Tyr-42, and β-Tyr-130). Table 3 lists the transition of MS$^3$ spectra.

TABLE 3

| AA start-end | peptides from α-globin | MS³ transitions |
|---|---|---|
| 17-31 | VGAHAGE$^{24}$Y$^{NO2}$GAEALER | 787.8 (+2) → 674.4 ($y_{12}'^{2+}$) → |
| 17-31 | VGAHAGE$^{24}$Y$^{NO}$GAEALER | 779.9 (+2) → 666.4 ($y_{12}'^{2+}$) → |
| 32-40 | $^{32}$M$^O$FLSFPTTK | 544.4 (+2) → 495.1 ($b_4'$) → |
| 41-56 | T$^{42}$Y$^{NO2}$FPHFDLSHGSAQVK | 940.0 (+2) → 817.5 ($b_{14}'^{2+}$) → |
| 62-90 | VADALTNAVAHVDD$^{76}$M$^O$PNALSALSDLHAHK | 1004.8 (+3) → 811.0 ($y_{15}'^{2+}$) → |
| 100-127 | LLSH$^{103}$C$^{O3}$LLVTLAAHLPAEFTPAVHASLDK | 1005.9 (+3) → 1283.4 ($y_{24}'^{2-}$) → |
| 100-127 | LLSH$^{104}$C$^{O2}$LLVTLAAHLPAEFTPAVHASLDK | 1000.5 (+3) → 702.9 ($b_{13}'^{2+}$) → |
| | peptides from β-globin | |
| 41-59 | FFESFGDLSTPDAV$^{35}$M$^O$GNPK | 1038.0 (+2) → 830.0 ($y_7'$) → |
| 83-95 | GTFATLSELH$^{93}$C$^{O3}$DK | 735.4 (+2) → 879.4 ($y_7'$) → |
| 105-120 | LLGNVLV$^{112}$C$^{O3}$VLAHHFGK | 884.5 (+2) → 1059.4 ($y_9'$) → |
| 121-132 | EFTPPVQAA$^{130}$Y$^{NO2}$QK | 712.4 (+2) → 1046.3 ($y_9'$) → |

Figure 5:
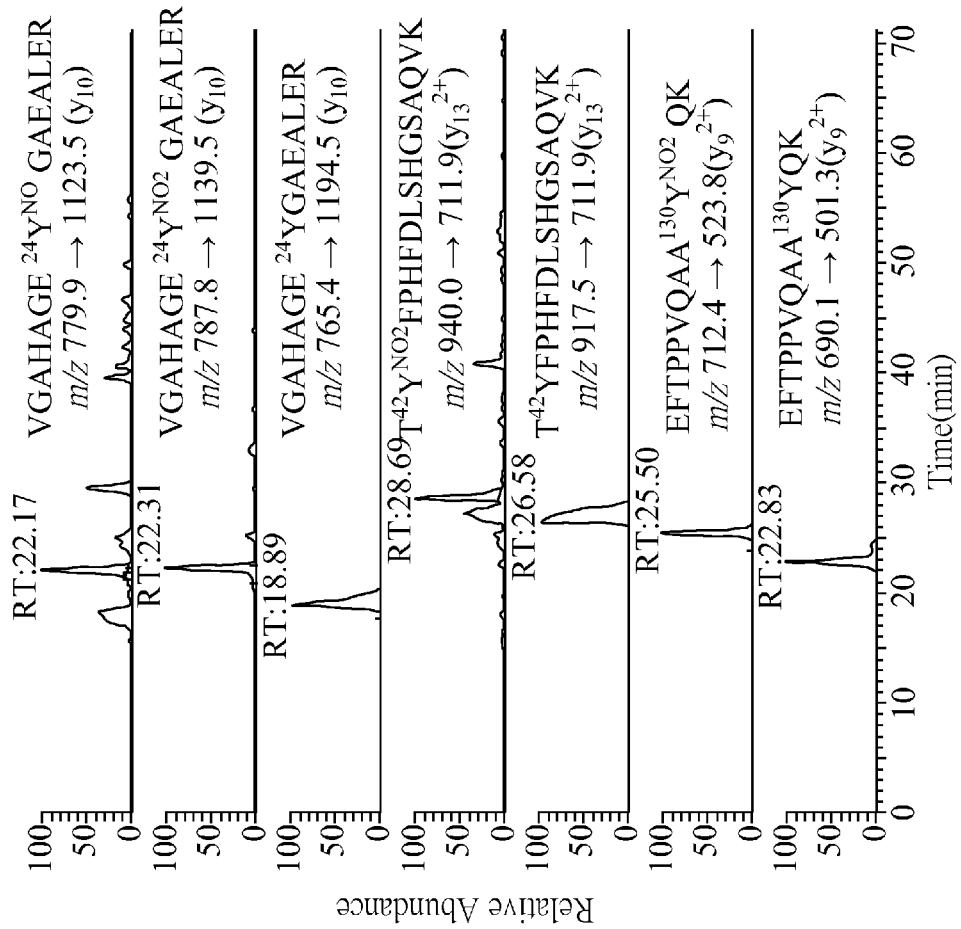
FIG. 5 shows nanoLC-MS/MS spectra of the nitration and the nitrosation of tyrosine of a preferred embodiment of the present invention.

As shown in FIG. 5, the elution time of the modified peptide is about 2 to 3 minutes later than that of the unmodified peptide, and the elution of α-Tyr-24 nitrosylated peptide is slightly earlier than that of the nitrated peptide. The extent of modification was represented by the ratio of peak area of modified peptide over the sum of all signal peak areas in LC-MS/MS chromatograms, wherein the sum of all signal peak areas includes the signal peak areas of modified and unmodified peptides.

Methionine Oxidation

In the reaction of hemoglobin sample with peroxynitrite, it shows that three methionine residues including Met-32, Met-76 and Met-55 are oxidized into sulfoxide.

Cysteine Oxidation

In the reaction of hemoglobin sample with peroxynitrite, it shows that modifications including the sulfonic acidification of cysteine oxide products such as α-Cys-104, β-Cys-93 and β-Cys-112 and the sulfinic acidification of α-Cys-104 are observed.

Post-Translational Modifications in Hemoglobin Isolated from Fresh Blood

A total of 40 human blood samples, including 20 smokers and 20 non-smokers, were analyzed for these 11 post-translational modifications by the nanoLC-NSUMS/MS using the SRM method. Only 10 μL of blood was required for human hemoglobin isolation. After the concentration of hemoglobin was quantified, 50 μg of hemoglobin was digested and 1/25 of the solution was subjected into the nanoLC-NSUMS/MS. In other words, only an equivalent of 0.01-0.02 μg of the hemoglobin sample was analyzed. Since the isolation process of hemoglobin relates to a precipitation process, therefore it is difficult to obtain a hemoglobin precipitate from the blood with a volume smaller than 10 μL.

Figure 6:
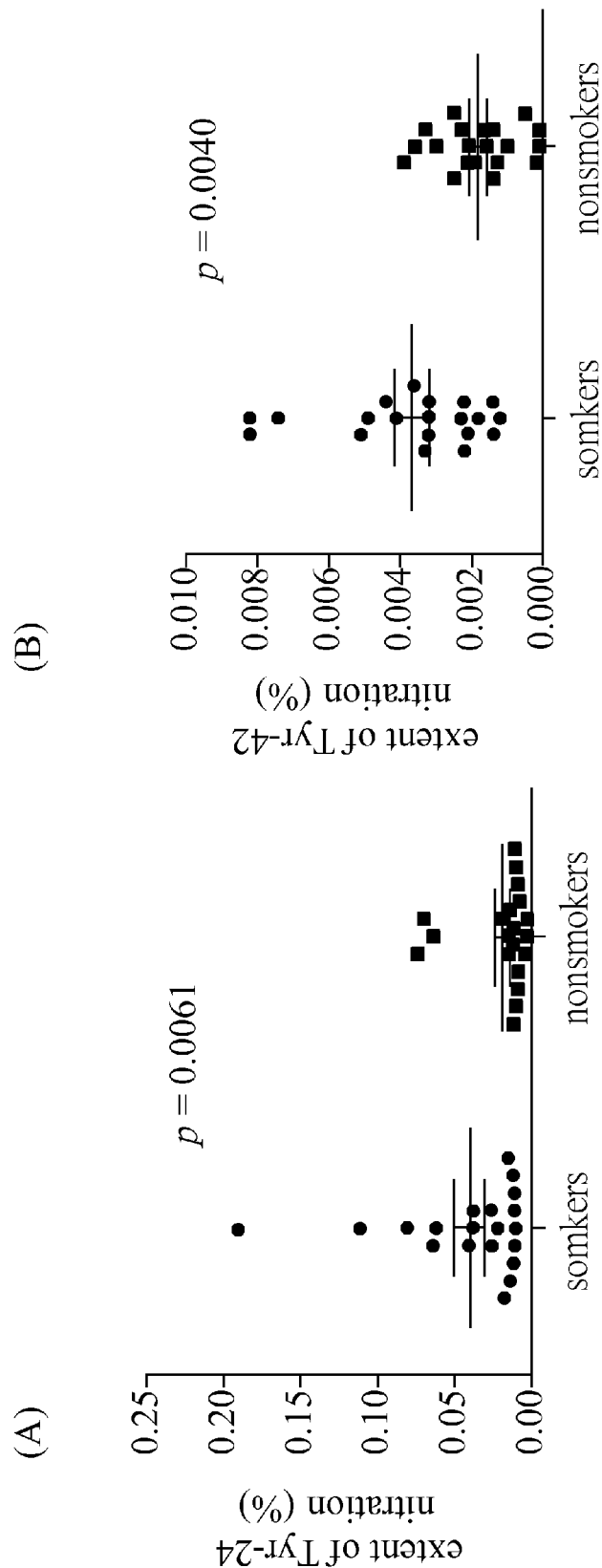
FIG. 6 shows the extent of nitration in smokers and non-smokers of a preferred embodiment of the present invention.

As shown in FIG. 6 and Table 4, the extents of nitration on α-Tyr-24 and α-Tyr-42 were significantly higher in smokers than in non-smokers [using the nonparametric Mann-Whitney test with p values of 0.0061 and 0.0040, respectively].

TABLE 4

| | extent of modification | | |
|---|---|---|---|
| | smokers (n = 20) | nonsmokers (n = 20) | p value$^a$ |
| $^{24}$Y$^{NO}$ | 0.016% ± 0.028% | 0.010% ± 0.012% | |
| $^{24}$Y$^{NO2}$ | 0.041% ± 0.045% | 0.019% ± 0.022% | 0.0061 |
| $^{42}$Y$^{NO2}$ | 0.0037% ± 0.0022% | 0.0018% ± 0.0012% | 0.0040 |
| $^{130}$Y$^{NO2}$ | 0.039% ± 0.068% | 0.017% ± 0.016% | |
| $^{32}$M$^O$ | 3.7% ± 1.1% | 4.2% ± 1.2% | |
| $^{76}$M$^O$ | 7.2% ± 2.6% | 8.5% ± 2.6% | |
| $^{55}$M$^O$ | 7.7% ± 2.9% | 9.5% ± 3.7% | |
| $^{104}$C$^{O3}$ | 0.037% ± 0.047% | 0.022% ± 0.021% | |
| $^{104}$C$^{O2}$ | 0.020% ± 0.016% | 0.021% ± 0.016% | |
| $^{93}$C$^{O3}$ | 0.58% ± 0.41% | 0.53% ± 0.37% | |
| $^{112}$C$^{O3}$ | 0.026% ± 0.028% | 0.013% ± 0.019% | |

In summation of the description above, the analytical method of the present invention not only achieves the effects of characterizing and quantifying various post-translational modifications of the hemoglobins and providing a high sensitivity, but also completes the analysis with a small quantity of test sample. In addition, the analysis result of the post-translational modification of nitration obtained by the analytical method of the present invention can be used as a biological indicator for evaluating the nitration pressure in a living organism, so as to diagnose and analyze smoking related diseases.

What is claimed is:

1. An analytical method of determining an extent of post-translational modifications in hemoglobin, comprising:
   providing a blood of a first group and a second group of samples wherein the first group of samples are from a test subject and the second group of samples are control samples, each comprising a hemoglobin, wherein the hemoglobin has a post-translational modification (PTM) of nitration;
   performing an extraction process to the blood by an organic solvent to obtain the hemoglobin;
   quantifying the hemoglobin by a fluorescent spectrometry;
   hydrolyzing the hemoglobin into a plurality of peptides by an enzyme;
   using a nanoflow liquid chromatography-nanospray ionization tandem mass spectrometry (nanoLC-NSI/MS/MS) to analyze the post-translational modifications of the hemoglobin according to tyrosine 24 and tyrosine 42 on α chain and tyrosine 130 on β chain of an amino acid sequence of the hemoglobin to obtain modification extents of the post-translational modifications of the first group and the second group, wherein the modification extents are represented by a ratio of a peak area of a modified peptide over a sum of all signal peak areas in a chromatogram obtained from the nanoLC-NSI/MS/MS, wherein the sum of all signal peak areas includes the signal peak areas of the modified and unmodified peptides, wherein a nanospray ionization tandem mass spectrometry of the nanoLC-NSI/MS/MS is LTQ linear ion trap mass spectrometry fitted with a nanospray ionization source; and comparing the modification extent of the post-translational modifications of the first group with that of the second group to determine the extent of modifications in the test subject.

2. The analytical method of post-translational modifications in hemoglobin according to claim 1, wherein the blood has a volume of 10 μL.

3. The analytical method of post-translational modifications in hemoglobin according to claim 1, wherein the enzyme is trypsin.

4. The analytical method of post-translational modifications in hemoglobin according to claim 1, wherein the nano-flow liquid chromatography-nanospray ionization tandem mass spectrometry has a spray voltage from 1.3 kV to 2.0 kV.

5. The analytical method of post-translational modifications in hemoglobin according to claim 1, wherein the nano-flow liquid chromatography-nanospray ionization tandem mass spectrometry has an ion transfer tube with a heating temperature from 200° C. to 300° C.

6. The analytical method of post-translational modifications in hemoglobin according to claim 1, wherein the nano-flow liquid chromatography-nanospray ionization tandem mass spectrometry further comprises collision energy, and the collision energy ranges from 10% to 35% after being normalized.

7. The analytical method of post-translational modifications in hemoglobin according to claim 1, wherein the nano-flow liquid chromatography-nanospray ionization tandem mass spectrometry has an analysis mode being a selected reaction monitoring (SRM) mode.

8. The analytical method of post-translational modifications in hemoglobin according to claim 1, wherein the modification extent of the post-translational modifications of the first group is higher than that of the second group if the first group and the second group are provided from a smoker and a non-smoker, respectively.

\* \* \* \* \*